(12) United States Patent
Froese et al.

(10) Patent No.: US 11,998,926 B2
(45) Date of Patent: Jun. 4, 2024

(54) SYSTEM AND METHOD FOR PROCESSING HEMP PLANTS AND PRODUCTS PRODUCED THEREBY

(71) Applicant: Mativ Holdings, Inc., Alpharetta, GA (US)

(72) Inventors: Hank Froese, Winkler (CA); Joaquin Mota, Winkler (CA)

(73) Assignee: Mativ Holdings, Inc., Alpharetta, GA (US)

( * ) Notice: Subject to any disclaimer, the term of this patent is extended or adjusted under 35 U.S.C. 154(b) by 150 days.

(21) Appl. No.: 17/491,912

(22) Filed: Oct. 1, 2021

(65) Prior Publication Data

US 2022/0105521 A1   Apr. 7, 2022

Related U.S. Application Data

(60) Provisional application No. 63/086,845, filed on Oct. 2, 2020.

(51) Int. Cl.
*B02C 13/04* (2006.01)
*B02C 23/08* (2006.01)
*B07B 1/28* (2006.01)

(52) U.S. Cl.
CPC ............... *B02C 23/08* (2013.01); *B02C 13/04* (2013.01); *B07B 1/28* (2013.01)

(58) Field of Classification Search
CPC ............ B02C 23/08; B02C 13/04; B07B 1/28

USPC ....................................................... 241/24.29
See application file for complete search history.

(56) References Cited

U.S. PATENT DOCUMENTS

| 2020/0253264 A1* | 8/2020 | Rousseau | A24D 1/20 |
| 2020/0253269 A1* | 8/2020 | Rousseau | A24B 15/16 |
| 2022/0105521 A1* | 4/2022 | Froese | B02C 13/04 |

FOREIGN PATENT DOCUMENTS

| AU | 2021351950 A1 * | 5/2023 | A61K 31/352 |
| CA | 3009554 A1 * | 3/2019 | A01G 22/00 |
| CA | 3009554 A1 | 3/2019 | |
| WO | WO-2021087314 A1 * | 5/2021 | A61K 36/185 |
| WO | WO-2022070165 A1 * | 4/2022 | A61K 31/352 |

OTHER PUBLICATIONS

International Search Report and The Written Opinion of the International Searching Authority, or the Declaration Corresponding to Application No. PCT/IB2021/059062 dated Jan. 12, 2022.

* cited by examiner

*Primary Examiner* — Terrell H Matthews
(74) *Attorney, Agent, or Firm* — Dority & Manning, P.A.

(57) ABSTRACT

A system and method for processing hemp plants is disclosed. The process is capable of processing whole *Cannabis* plants for producing multiple useful products. A pair of hammermills are used in series in order to produce an extractable *Cannabis* material for obtaining cannabinoids, such as CBD and a fiber product. The hurds contained in the *Cannabis* plant material are controlled and fractionated during the process for allowing high throughput.

12 Claims, 2 Drawing Sheets

SYSTEM AND METHOD FOR PROCESSING HEMP PLANTS AND PRODUCTS PRODUCED THEREBY

RELATED APPLICATIONS

The present application is based upon and claims priority to Provisional Patent Application Ser. No. 63/036,845, having a filing date of Oct. 2, 2020, and which is incorporated herein by reference.

BACKGROUND

*Cannabis*, or the *Cannabis* plant, may refer to both marijuana, which is generally used for recreational purposes, and hemp, which is generally used in industrial applications. *Cannabis* is a green and/or brown mixture of dried, shredded leaves, stems, seeds and flowers of the plant, and may reference leaves, stems, seeds, stalks, and flowers from a *Cannabis* plant, varieties of which include *Cannabis sativa* or *Cannabis indica*. Hemp (and particularly the industrial hemp variety), has a very similar appearance to marijuana, but unlike the *Cannabis* plant variety referred to by marijuana, hemp generally only contains low amounts of tetrahydrocannabinol (THC), where both hemp and marijuana can include high amounts of cannabidiol (CBD). For instance, industrial hemp may contain less than about 0.3% THC where the *Cannabis* variety referred to by marijuana may contain anywhere from 5% to 30% THC. Recently, over 25 states in the United States have legalized the use of *Cannabis* for at least medical purposes. In addition, Canada has now legalized the use of *Cannabis* for medical and recreational use. In view of these recent developments, the commercialization of *Cannabis* has dramatically increased.

*Cannabis*, for instance, is becoming a more and more popular drug for pain relief in lieu of conventional pain relief medicines, such as opioids. Opioids are powerful pain relief medications that relieve pain by acting on the nervous system. They are typically used to treat severe pain after surgery and are also used to treat chronic pain. Unfortunately, however, opioids come with many risks. For example, opioids are highly addictive which has led to an epidemic of drug misuse. In fact, more than 11 million people each year misuse prescription opioids.

In view of the legalization and popularity of *Cannabis* over a wide variety of applications, a need exists for a way to quickly process the plant material at high throughput rates. Currently, commercial decortication processes exist that are capable of processing bales of hemp plant in order to primarily separate the fiber for the rest of the plant material. *Cannabis* and hemp plants include a plant stalk that includes an outer skin layer and an inner core primarily made of hurd. The bast fiber of the plant is located within the skin and is generally the more valuable commodity. Once processed according to a decortication process, the components of *Cannabis* and hemp plants include the bast fiber, the hurd, short fiber, and dust. Each of these components has application for use in a variety of consumer, commercial and industrial products. Each of the above products, for instance, can be used to produce paper, particle board, construction composites, animal bedding, industrial absorbents, textiles, and the like. Although current decortication processes are well suited for removing and separating the above described materials, particularly the bast fibers, such processes are not well suited to extracting chemical components, such as cannabidiols from the *Cannabis* and hemp plants. Chemical components such as cannabidiols, for instance, are typically removed from *Cannabis* and hemp plants using an extraction process that may render the fibers unusable. Alternatively, the extraction processes may only be designed to extract chemical components from the leaves and flowers of the plant without extracting the chemical components from the remainder of the plant.

In essence, there are commercial processes available for extracting fibers from *Cannabis* and hemp plants and there are other processes designed to extract chemical components from the plants. What is needed, however, is a commercial process capable of not only separating fibers from the *Cannabis* and hemp plants but also capable of simultaneously removing and separating the materials of the plant that contain the greatest amounts of the chemical components, such as cannabidiols and the like.

SUMMARY

In general, the present disclosure is directed to a process and system for processing *Cannabis* plants in order to efficiently separate the plants into different fractions that each represent a valuable raw material for use in a variety of applications. For instance, the process of the present disclosure can be used to separate the *Cannabis* plant material into structural components, such as fibers and shives and into extractable components well suited for use in extraction processes for removing valuable chemical components from the plant. The process and system of the present disclosure can be operated at very high throughput rates without producing any significant waste products.

In one embodiment, for instance, the present disclosure is directed to a method for processing *Cannabis* plants. The method includes feeding cut and dried *Cannabis* plants to at least one hammermill and decorticating the hemp plants to form a fiber material stream and a *Cannabis* material stream, the fiber material stream containing *Cannabis* hurds in an amount from about 20% to about 55% by weight, the *Cannabis* material stream containing *Cannabis* hurds in an amount from about 2% to about 15% by weight. The *Cannabis* material stream further comprises a blend of shreds and fines, the shreds and fines comprise *Cannabis* leaves, *Cannabis* buds, and the *Cannabis* hurds. The method further includes collecting the *Cannabis* material stream. The fiber material stream is then fed to at least one further downstream hammermill and screened to remove *Cannabis* hurds and fines and to form a fiber tow The fiber tow can be baled. The fiber tow can contain *Cannabis* hurd in an amount less than about 10% by weight.

In one aspect, the dried *Cannabis* plants can be in the form of bales and the method can further include the step of breaking the bales apart prior to feeding the cut and dried *Cannabis* plants to a first hammermill. The decorticated hemp plants can be fed to a screening device during or after being fed through the first hammermill for forming the fiber material stream and the *Cannabis* material stream.

Optionally, the fiber material stream can then be fed to a second hammermill. In the second hammermill, the fiber material stream can be further subjected to decortication and hammering in order to further break apart and loosen the materials within the fiber material stream. In one aspect, the second hammermill can be operated without creating a side product stream. Thus, 100% or substantially all of the fiber material stream that enters the second hammermill also exits the second hammermill within the same stream. From the second hammermill, the fiber material stream can be fed to a second screening device for separating small particles and fines from the fiber material stream. The small particles and fines can be combined with the *Cannabis* material stream.

The *Cannabis* material stream as described above can then be processed for removing one or more cannabinoids.

In one embodiment, the method or process can further include the step of extracting one or more cannabinoids from the *Cannabis* material stream. The *Cannabis* material stream can contain *Cannabis* hurds in an amount from about 7% to about 12% by weight.

In general, any suitable *Cannabis* plant can be processed according to the present disclosure. For instance, the *Cannabis* plant may comprise *Cannabis indica, Cannabis sativa*, or mixtures thereof.

In the first part of the process as described above, in order to produce the *Cannabis* material stream, the process is optimized in order to limit the amount of hurds contained in the *Cannabis* material. In the second part of the process, the system is optimized in order to produce a fiber tow stream that contains little to no hurds.

In one aspect, for instance, the fiber material stream, after separating and collecting the *Cannabis* material stream, is then fed to one or more further hammermills in order to produce a fiber tow. In one aspect, for instance, the fiber material stream is fed to a third hammermill in which the fiber material stream is further hammered and pressed against a screen for removing non-fibrous material that forms a first shive stream. From the third hammermill, the fiber material stream can then optionally be fed to a third screening device for further removing fines and other non-fibrous particles that can then form a second shive stream. From the third screening device, the fiber material stream can be collected as a fiber tow.

Optionally, the fiber material stream exiting the third screening device can be fed to a fourth hammermill for further processing the fiber material stream and removing greater amounts of hurds and other non-fibrous material. The fourth hammermill, for instance, can form a third shive stream. From the fourth hammermill, the fiber material stream can optionally be fed to a fourth screening device. The fourth screening device can be a shaker device or include agitation for removing as much fines and dust from the fiber product stream as possible.

From the fourth screening device, a fiber tow stream is created that can be collected and used in numerous applications as a source of fiber.

The different shive streams can be accumulated and collected as a shive product.

Consequently, the process of the present disclosure can be used to produce a *Cannabis* product, a fiber tow product, and a shive product.

As described above, the method of the present disclosure permits very high throughputs. For instance, in one embodiment, the method can process greater than about 5 metric tons per hour, such as greater than about 8 metric tons per hour, such as greater than about 10 metric tons per hour, such as greater than about 12 metric tons per hour of the cut and dried *Cannabis* plants.

The present disclosure is also directed to a plant product that can be produced by the method described above. The plant product of the present disclosure comprises a *Cannabis* material containing a blend of shreds and fines. The shreds and fines comprise *Cannabis* leaves, *Cannabis* buds, and *Cannabis* hurds. The *Cannabis* material may also contain *Cannabis* flowers. In accordance with the present disclosure, *Cannabis* hurds are present in the plant product in an amount from about 2% to about 15% by weight. For instance, the *Cannabis* hurds can be present in the product in an amount greater than about 3% by weight, such as in an amount greater than about 5% by weight, such as in an amount greater than about 8% by weight, and generally In an amount less than about 13% by weight, such as in an amount less than about 11% by weight. The above plant product is particularly well suited to being used as a raw material for obtaining chemical compounds from the *Cannabis* plants, such as cannabinoids. The amount of hurds present in the product allows for efficient collection of the *Cannabis* material while still providing a product that has significant valuable extracts contained therein, such as cannabinoids.

The *Cannabis* material can generally contain shreds in an amount from about 30% to about 90% by weight and fines in an amount from about 10% to about 70% by weight. The shreds can include plant pieces having a largest dimension of greater than about 1.5 cm, such as greater than about 2 cm, and less than about 8 cm, such as less than about 6 cm. The *Cannabis* material can be initially collected such that none of the *Cannabis* material has been extracted. Once collected, the *Cannabis* material can be subjected to further sorting processes and/or grinding processes and subjected to one or more extraction processes for extracting various chemical components, such as one or more cannabinoids.

The *Cannabis* material can generally contain moisture in an amount less than about 20% by weight, such as in an amount less than about 15% by weight, such as in an amount less than about 10% by weight, such as in an amount less than about 8% by weight. The *Cannabis* material can contain one or more cannabinoids in an amount greater than about 5% by weight such as in an amount greater than about 10% by weight.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
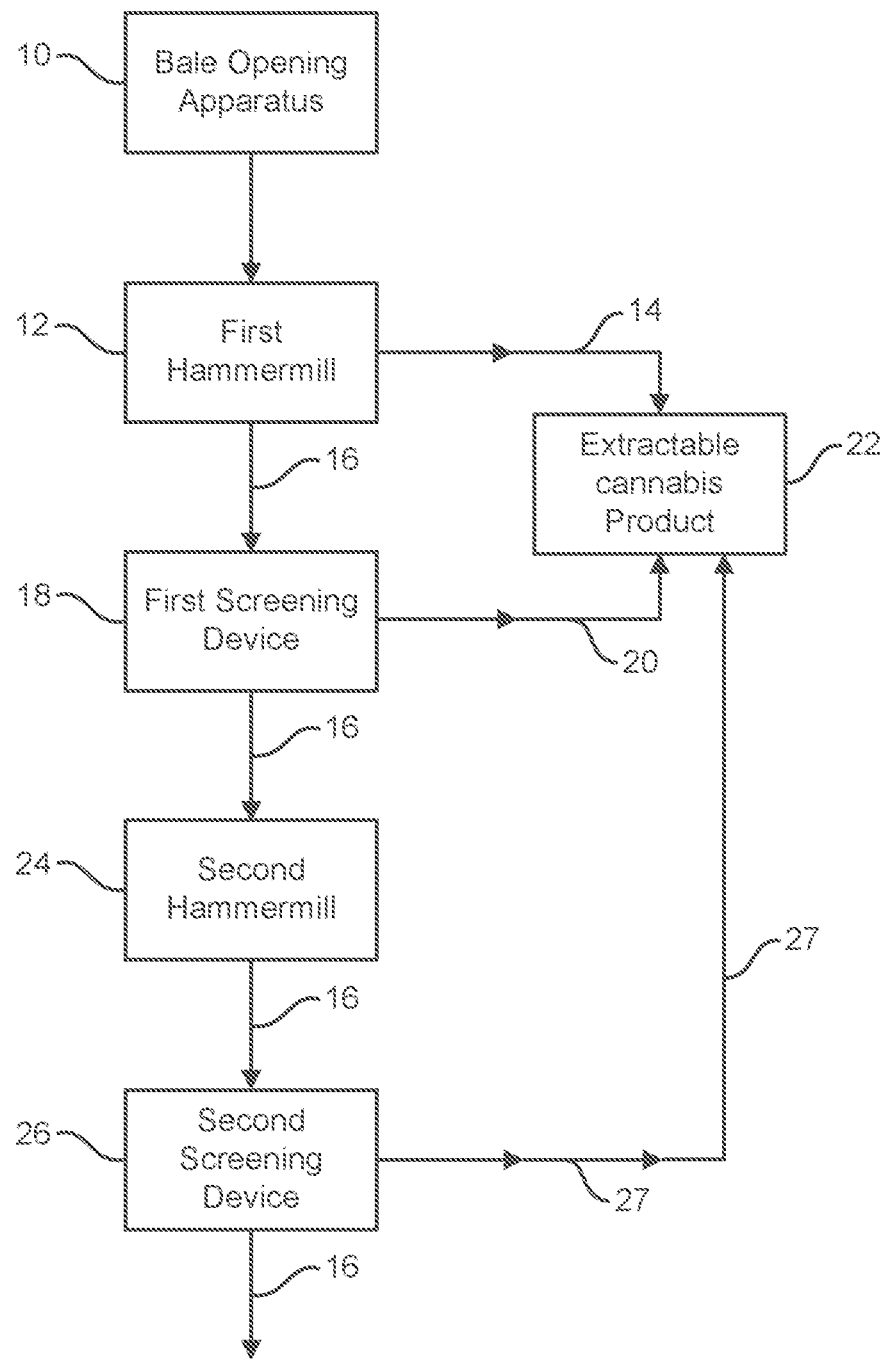
FIG. 1 is a block diagram illustrating one embodiment of the method of the present disclosure.

Repeat use of reference characters in the present specification and drawings is intended to represent the same or analogous features or elements of the present invention.

Definitions

As used herein, "*Cannabis*" may refer to any variety of the *Cannabis* plant, such as *Cannabis sativa* or *Cannabis indica*, for instance. More particularly, the present disclosure may refer to leaves, stems, seeds, stalks and flowers or any other part of the *Cannabis* plant, as *Cannabis*. Nonetheless, *Cannabis*, as referred to herein, includes *Cannabis* that contains average or high levels of THC and/or CBD (usually known as marijuana), hemp, which may contain low, or very low, levels of THC, industrial hemp, which may refer to a *Cannabis* plant that contains less than 0.3% THC, or combinations thereof.

As used herein, the term "stalk" is used to refer to the main structural portion of a plant that remains after the leaves have been removed.

As used herein, the term "hurd" is used herein to refer to the structural portion of a plant, (e.g. inner portion of the stalk) connecting the leaves or laminae to the stalk and also may include portions of the veins or ribs that extend through the leaves.

DETAILED DESCRIPTION

It is to be understood by one of ordinary skill in the art that the present discussion is a description of exemplary embodiments only and is not intended as limiting the broader aspects of the present disclosure.

In general, the present disclosure is directed to a system and method for processing *Cannabis* plants. Through the process of the present disclosure, intact and whole *Cannabis* plants can be rapidly processed into multiple different useable products. For example, the process is capable of isolating and collecting *Cannabis* or hemp fibers. In addition, during the process, a *Cannabis* material is also collected containing *Cannabis* leaves, *Cannabis* buds, and/or *Cannabis* flowers that is well suited to being subjected to an extraction process for extracting various chemical components from the *Cannabis* plants, including pain relieving pharmaceuticals, such as cannabinoids. The process of the present disclosure can also produce a shive product stream that can be used in multiple different applications such as animal bedding, biomass incineration, or the like.

Not only does the process and system of the present disclosure convert whole *Cannabis* plants into multiple useful product streams without creating waste, but also can do so at extremely high throughputs. For instance, the process of the present disclosure is capable of processing greater than about 5 metric tons per hour of *Cannabis* plants, such as greater than about 8 metric tons per hour, such as greater than about 10 metric tons per hour, such as greater than about 12 metric tons per hour, such as greater than about 14 metric tons per hour of *Cannabis* plants. In one application, for instance, the process and system is capable of processing from about 12 metric tons per hour to about 25 metric tons per hour using a single process line.

Referring to FIG. 1, one exemplary embodiment of a process in accordance with the present disclosure is shown. Although the process of the present disclosure can process any part of the hemp or *Cannabis* plant, in one embodiment, the process is designed to receive the whole plant material. For example, in one embodiment, bales of *Cannabis* or hemp plants are delivered to the processing facility (although mobile units are also possible). The whole *Cannabis* plants can include, for instance, stalks, leaves, buds, flowers, and any other parts of the plant.

In one aspect, the hemp or *Cannabis* plants have been at least partially dried. For example, the hemp plants processed according to the present disclosure can have a moisture content of generally less than about 19%, such as less than about 17%, such as less than about 15%, such as less than about 13%, such as less than about 11%. The moisture content is generally greater than about 5%, such as greater than about 8%. Although the process and system can handle plants with higher moisture content, if desired, the plants can be subjected to a drying process prior to entering the process if moisture content levels are relatively high. The plants can be dried by either being placed in the open air or fed through an oven at relatively mild temperatures, such as at temperatures of less than about 90° C., such as at temperatures less than about 80° C., and generally at temperatures greater than about 40° C., such as temperatures greater than 60° C.

When the starting *Cannabis* plant material is in the form of bales, as shown in FIG. 1. the process and system can include a bale opening apparatus 10. In general, any suitable bale opening apparatus 10 may be used, in one aspect, for instance, the bale opening apparatus can include an input conveyor for receiving the bales of *Cannabis* plants. The conveyor can convey the bales to a moving spiked device that includes a rotatable drum. If desired, the bale opening apparatus 10 can also include a crushing device for pre-crushing the plants prior to entry into the processing system downstream.

After the bales of *Cannabis* plants have been opened, the *Cannabis* plant material is fed to a first hammermill 12 as shown in FIG. 1. The hammermill 12 is particularly designed to receive whole plants. More particularly, the hammermill 12 is configured to receive not only stalks but also leaves, buds, and any other parts of the *Cannabis* plant.

The hammermill 12 generally includes a rotating drum contained within a shell. The rotating drum includes a plurality of hammers that are spread over the surface of the rotating drum. In one embodiment, each hammer can be pivotably mounted to the drum. The drum is then surrounded by a housing Hammermill 12, for instance, can include a drum that is surrounded by a screen.

The whole *Cannabis* plants are fed into the hammermill 12 between the rotating drum and the screen. As the plant material enters the hammermill 12, the hammers on the drum pivot outwardly and contact the plant material against the screen. In this manner, the hammermill 12 crushes the plant and separates it into different components. More particularly, the first hammermill 12 produces a *Cannabis* material stream 14 and a fiber material stream 16. The *Cannabis* material stream 14 includes the *Cannabis* plant material that filters through the screen of the hammermill 12. The fiber material stream 16, on the other hand, represents the plant material that does not filter through the screen and instead is fed downstream.

The *Cannabis* material stream 14 generally contains the leaves, stems, buds, flowers, and any other more fragile material contained on the *Cannabis* plant. The *Cannabis* material stream 14 can also contain portions of the *Cannabis* stalk. The *Cannabis* stalk, for instance, includes a woody soft core surrounded by fibers, typically referred to as bast fibers. The material in the core surrounding the fibers is typically referred to as hurd and/or shive. The fibers generally represent from about 18% by weight to about 35% by weight of the stalk, and more particularly from about 22% by weight to about 28% by weight of the stalk. The remainder represents hurd. During decortication processes, the object and goal is typically to separate the fibers from the hurd as quickly and efficiently as possible. According to the present disclosure, however, the hurd contained in the *Cannabis* plants is carefully controlled and manipulated throughout the process. For example, not only is hurd not desirable in the fiber stream, but also may not be desirable in the *Cannabis* material stream 14 either. Hurd generally contains lesser chemical components, such as cannabinoids, than the leaves, buds, and flowers. The present disclosure is directed to fractionally dividing the hurds into the different streams so as to produce multiple products in a very fast and efficient way without the hurds reducing the value of the final products.

In this regard, the first hammermill 12 is operated so that a portion of the hurds enters the *Cannabis* material stream 14, while most of the hurds remain with the fibers in the fiber material stream 16. Consequently, in one aspect, the present disclosure is directed to a process in which the hurds are fractionated in a manner that maximizes efficiency without any adverse effects on the final product streams. For instance: the *Cannabis* material stream 14 generally contains hurds in an amount greater than about 2% by weight, such as in an amount greater than about 4% by weight, such as in an amount greater than about 6% by weight, such as in an amount greater than about 8% by weight, and generally in an amount less than about 20% by weight, such as in an amount less than about 17% by weight, such as in an amount less than about 15% by weight, such as in an amount less than about 13% by weight, such as in an amount less than about 12% by weight, such as in an amount less than about 10% by weight, such as in an amount less than about 8% by weight. The fiber material stream 16, on the other hand, generally contains hurds in an amount from about 20% to about 55% by weight, including all increments of 1% by weight therebetween. For example, the fiber material stream 16 can contain hurds in an amount greater than about 25% by weight, such as in an amount greater than about 30% by weight, such as in an amount greater than about 35% by weight, and generally in an amount less than about 50% by weight, such as in an amount less than about 45% by weight.

As shown m FIG. 1, after the first hammermill 12, the fiber material stream 16 can optionally be fed to a first screening device 18. The fiber material stream 16 can be fed to the first screening device 18 using flowing air as the carrier gas. The screening device 18 includes one or more sieves that separate out from the fiber material stream 16 any fines or small particles. The separation can occur at relatively high gas velocities. As used herein, a screening device can be any suitable device for separating smaller particles from larger particles. The screening device may include an apparatus where a high velocity fluid, such as air, impinges on one or more screens for separating the different materials. Alternatively, the screening device may operate using a centrifugal force. In still another embodiment, the screening device may operate using agitation or a shaking motion that causes materials to separate through a permeable barrier, such as a screen, e.g. mesh or sieve. The first screening device 18 produces a small particle stream 20 that can be combined with the Cannabis material stream 14 to form an extractable Cannabis product 22.

After the first hammermill 12 and optionally after the first screening device 18, the extractable Cannabis product 22 can be collected and processed for its chemical contents. In one aspect, however, the fiber material stream 16 can be further processed in order to collect more materials for the extractable Cannabis product 22.

For example, as shown in FIG. 1, in one embodiment, the fiber material stream 16 exiting the first screening device 18 can be fed to a second hammermill 24. The fiber material stream 16, for instance, can be gravity fed into the second hammermill 24. The second hammermill 24 is designed to further break up the fiber material stream 16 in order to remove hurds from the Cannabis fibers and/or to further separate the Cannabis fibers from extractable Cannabis material, such as leaves, flowers and buds. In one aspect, the second hammermill 24 can include a larger motor and subject the fiber material stream 16 to more energy than experienced in the first hammermill 12. Otherwise, the second hammermill 24 can operate similar to the first hammermill 12 and can include a plurality of pivoting hammers mounted on a rotating drum. The fiber material stream 16 enters the second hammermill 24 and is subjected to energy against the housing causing the fibers to separate from any other materials contained in the material stream.

The rotating drum contained m the second hammermill 24 can be surrounded by a screen for separating plant material from the plant fibers or alternatively can be surrounded by a non-perforated housing. For instance, in one aspect as shown in FIG. 1, only a single fiber material stream 16 exits the second hammermill 24 without creating a separate byproduct stream.

As shown in FIG. 1, in one embodiment, the fiber material stream exiting the second hammermill 24 can then be fed to a second screening device 26. The fiber material stream 16, for instance, can be air fed to the second screening device 26. The second screening device 26 can be designed to separate the Cannabis fibers from other plant material and form a small particle stream 27. The small particle stream 27 can be added to the extractable Cannabis product 22 if desired.

The extractable Cannabis product 22 is the first product produced by the process. The extractable Cannabis product generally contains a blend of plant shreds combined with fines. The fines can come from the small particle stream 20 or can also originate from the first hammermill 12. The plant shreds are the product that exits the first hammermill 12.

The shreds contained in the extractable cannabis product can have irregular sizes over a relatively wide size distribution. At least some of the shreds have a largest dimension of greater than about 1.5 cm and generally less than about 8 cm, including all increments of 0.5 cm therebetween. For instance, the shreds can have a largest dimension of greater than about 2 cm, such as greater than about 3 cm, such as greater than about 4 cm, and generally less than about 6 cm, such as less than about 5 cm.

The amount of fines in comparison to the amount of other material contained in the extractable Cannabis product 22 can vary depending upon the feed material and the process conditions. In general, the extractable Cannabis product can contain fines generally in an amount from about 10% to about 90% by weight, including all increments of 5% therebetween. For example, the extractable Cannabis product 22 can contain fines in an amount greater than about 10%, such as in an amount greater than about 15%, such as in an amount greater than about 20%, and generally in an amount less than about 70% by weight, such as in an amount less than about 50% by weight, such as in an amount less than about 40% by weight, such as in an amount less than about 30% by weight.

In an alternative embodiment, the fines from the first screening device are not combined with the extractable Cannabis product 22. In this embodiment, the extractable Cannabis product 22 can be collected so as to minimize the amount of fines. For example, the extractable Cannabis product 22, in one aspect, can contain fines in an amount less than about 10% by weight, such as in an amount less than about 8% by weight, such as in an amount less than about 6% by weight, such as in an amount less than about 4% by weight, such as in an amount less than about 2% by weight, such as in an amount less than about 1% by weight.

The extractable Cannabis product contains Cannabis leaves, Cannabis buds, and/or Cannabis flowers. As described above, the extractable Cannabis product also contains Cannabis hurds in an amount that does not significantly affect the value of the product and the ability to remove extractable components from the Cannabis plant material. For instance, the extractable Cannabis product 22 can contain hurds generally in an amount from about 2% to about 15% by weight, including all increments of 1% therebetween. In general, the extractable Cannabis product contains hurds in an amount less than about 12% by weight, such as in an amount less than about 10% by weight.

Through the process of the present disclosure, the extractable Cannabis product 22 has been found to be well suited for later processing into an extraction process for removing chemical components. *Cannabis* plants, for instance, contain various cannabinoids that can be used for pain relief. In accordance with the present disclosure, the extractable *Cannabis* product 22 is particularly well suited for releasing cannabinoids in an extraction process.

Cannabinoids that are contained in *Cannabis* plants include cannabidiol (CBD) and tetrahydrocannabinol (THC). THC contained in *Cannabis* acts on specific receptors in the brain which lead to a feeling of euphoria and a relaxed state. CBD, on the other hand, also interacts with pain receptors in the brain but does not create the same euphoric feeling caused by THC. In general, most *Cannabis* plants contain relatively high levels of CBD, such as *Cannabis sativa* or *Cannabis indica*. Industrial hemp, on the other hand, although containing ample quantities of CBD generally contains low levels of THC. Industrial hemp, for instance, typically contains THC in an amount less than 0.3% by weight. Either plant can be processed according to the present disclosure for removing CBD from the plant material and/or THC.

The extractable *Cannabis* product 22 collected in accordance with the present disclosure, for instance, can contain CBD in an amount greater than about 2% by weight, such as in an amount greater than about 5% by weight, such as in an amount greater than about 10% by weight, such as in an amount greater than about 15% by weight, and generally in an amount less than about 25% by weight, such as in an amount less than about 20% by weight. The extractable *Cannabis* product 22 can contain THC in one embodiment in an amount less than 0.3% by weight. In an alternative embodiment, the extractable *Cannabis* product 22 can contain THC in an amount greater than about 8% by weight, such as in an amount greater than about 10% by weight, such as in an amount greater than about 12% by weight, such as in an amount greater than about 15% by weight, and generally in an amount less than about 35% by weight, such as in an amount less than about 30% by weight, such as in an amount less than about 25% by weight.

In addition to THC and CBD, *Cannabis* plants can also contain various other cannabinoids. For instance, other cannabinoids contained in *Cannabis* include cannabichromene, cannabinol, cannabigerol, tetrahydrocannabivann, cannabidivarin, cannabidiolic acid, other cannabidiol derivatives, and other tetrahydrocannabinol derivatives. Any and all of these cannabinoids can be obtained from the extractable *Cannabis* product 22 of the present disclosure as desired.

The different chemical components can be obtained from the extractable *Cannabis* product 22 using any suitable process. In one aspect, the extractable *Cannabis* product 22 can be further ground or sized if desired. The extractable *Cannabis* product 22 can then be subjected to an extraction process, such as a fluid extraction process. In general, a suitable fluid, which is typically in a liquid state, is applied as an extracting solvent to the plant material for carrying out the extraction. The extractable *Cannabis* product 22, for instance, can first be contacted with water and then contacted with an extracting solvent by mixing together in a suitable apparatus. A carrier liquid which contains the desired component from the *Cannabis* plant material is then removed and converted into a final product.

Suitable extraction processes include liquid-liquid extraction or can include supercritical fluid extraction. In still another aspect, a conventional solvent extraction can take place. The extractable *Cannabis* product 22 has been found particularly well suited to producing a CBD oil, a THC oil, or any other cannabinoid extract.

The fiber material stream 16 exiting the second screening device 26 generally contains significant amounts of hurd in combination with a valuable fiber product. Once the extractable *Cannabis* product 22 is separated from the fiber material stream 16, the fiber material stream 16 can be further processed in order to collect a fiber tow in which the fibers have been substantially or completely separated from other plant material. In one aspect, for instance, the fiber material stream 16 can be fed to one or more hammermills in order to further break up the fiber material stream and separate the fibers from other plant materials. For example, the fiber material stream can be fed through a single hammermill and/or screening device or can be fed through more than one hammermill, such as through a plurality of hammermills in order to collect the *Cannabis* fibers.

Figure 2:
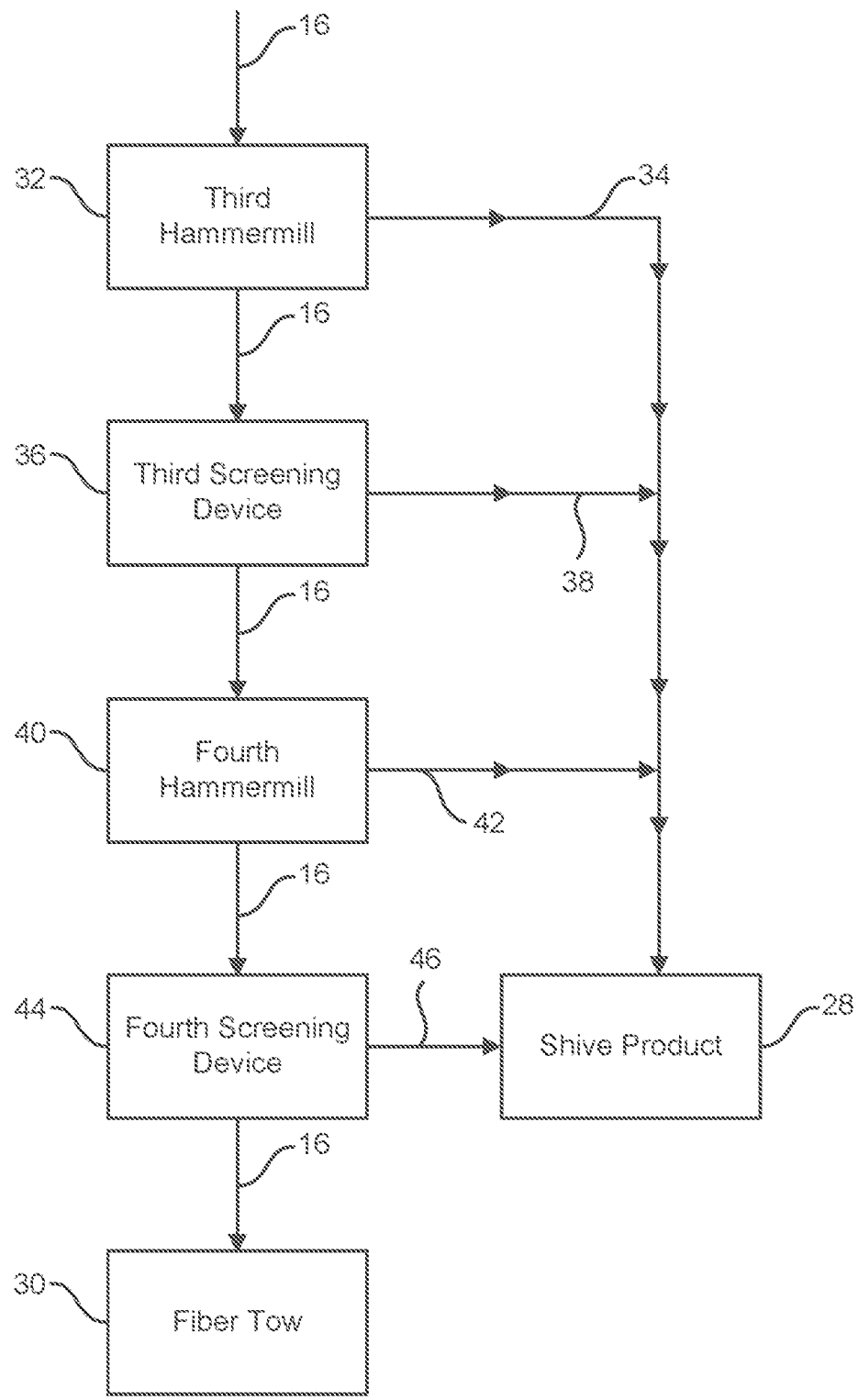
FIG. 2 is a block diagram illustrating optional further process steps that may be combined with the method illustrated in FIG. 1.

Referring to FIG. 2, for instance, one embodiment of a process according to the present disclosure is shown in which the fiber material stream 16 is further fed to two hammermill devices for producing a fiber product. As shown in FIG. 2, for instance, the fiber material stream 16 is fed to a third hammermill 32 The third hammermill 32 is designed to further separate the *Cannabis* fibers from the hurd. The third hammermill 32, for instance, can include a plurality of pivoting hammers mounted on a rotating drum that is surrounded by a housing comprising a screen. Smaller particles, such as hurds, fit through the screen and form a shive material stream 34.

From the third hammermill 32 the fiber material stream can then be fed to a third screening device 38 where further smaller particles can be removed to form a shive material stream 38. In the embodiment illustrated in FIG. 2, the fiber material stream exiting the third screening device 36 is then fed to a fourth hammermill 40. The fourth hammermill 40 can further break up the fiber material stream for removing hurds and other plant matter from the plant fibers and form an additional shive material stream 42. From the fourth hammermill 40, the fiber material stream 16 can optionally be fed to a fourth screening device 44. In one aspect, the fourth screening device 44 can be a shaker device that subjects the fiber material stream 16 to agitation for removing as much plant matter as possible from the plant fibers. The fourth screening device 44, for instance, can further form another shive material stream 46.

As shown in FIG. 2. the shive material streams 34, 38, 42 and 46 can be combined to form and collect a shive product 28. The fiber material stream 16 exiting the fourth screening device, on the other hand, can form a fiber tow product 30.

The fiber tow product 30 can essentially contain only *Cannabis* fibers and can be baled and sold for multiple different applications. The fiber tow product 30, for example, can contain hurds in an amount less than 10% by weight, such as in an amount of less than about 8% by weight, such as in an amount of less than about 4% by weight, such as in an amount of less than about 2% by weight, such as in an amount of less than about 1% by weight. The *Cannabis* fibers, for instance, can be used in textile applications, to produce rope, to reinforce other materials, and the like.

The shive product 28, on the other hand, generally contains hurds and other plant matter. The shive product 28 can be used for animal bedding, oil absorbency: and the like.

During the process, various other devices can be used to help facilitate collection of the different materials. For example, in one aspect, baghouses can be used in order to collect fines and combine them with the other product streams.

Through the process and system of the present disclosure, entire *Cannabis* plants can be processed and converted into at least three different useful products without creating waste. The process and system allows for a very fast and efficient method for obtaining an extractable and unique *Cannabis* product that is rich in cannabinoids, such as CBD in this manner, a CBD rich product can be produced and collected at extremely high throughputs. In addition, not only is a product produced rich in CBD but also the *Cannabis* or hemp fibers are isolated and baled and can be used in many different useful applications These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only and is not intended to limit the invention so further described in such appended claims.

What is claimed:

1. A method for processing *cannabis* plants comprising:
   feeding cut and dried *cannabis* plants to a first hammermill and decorticating the *cannabis* plants to form a fiber material stream and a *cannabis* material stream, the fiber material stream containing *cannabis* hurds in an amount of from about 20% to about 55% by weight, the *cannabis* material stream containing *cannabis* hurds in an amount from about 2% to about 15% by weight, the *cannabis* material stream further comprising a blend of shreds and fines, the shreds and fines comprising *cannabis* leaves, *cannabis* buds, and the *cannabis* hurds;
   collecting the *cannabis* material stream;
   feeding the fiber material stream to a second hammermill and screening the fiber material stream to remove *cannabis* hurds and fines to form a fiber tow; and
   baling the fiber tow, the fiber tow containing *cannabis* hurd in an amount less than about 10% by weight.

2. A method as defined in claim 1, wherein the method processes greater than about 5 metric tons per hour of cut and dried *cannabis* plants.

3. A method as defined in claim 1, wherein the dried *cannabis* plants are in the form of bales and the method further includes breaking the bales apart prior to feeding the cut and dried *cannabis* plants to the first hammermill.

4. A method as defined in claim 1, wherein the decorticated *cannabis* plants are fed to a screening device during or after being fed through the first hammermill for forming the fiber material stream and the *cannabis* material stream.

5. A method as defined in claim 1, wherein the *cannabis* hurds and fines removed from the fiber material stream are collected to form a shive product.

6. A method as defined in claim 1, further comprising the step of extracting one or more cannabinoids from the *cannabis* material stream.

7. A method as defined in claim 1, wherein the *cannabis* plants comprise *Cannabis* indica plant material.

8. A method as defined in claim 1, wherein the dried *cannabis* plants comprise *Cannabis sativa* plant material containing less than 0.3% by weight tetrahydrocannabinol.

9. A method as defined in claim 1, wherein the *cannabis* material stream contains *cannabis* hurds in an amount from about 7% to about 12% by weight and wherein the fiber material stream contains *cannabis* hurds in an amount from about 32% to about 49% by weight.

10. A method as defined in claim 1, wherein the fiber material stream is gravity fed to the second ham merm ill.

11. A method as defined in claim 1, wherein the fiber material stream is air conveyed to a screening device for screening the fiber material stream.

12. A method as defined in claim 1, wherein the fiber material stream is further fed to a third ham merm ill and then to a fourth hammerm ill in order to further break apart the fiber material stream and separate the fiber material stream from *cannabis* hurds and fines.

\* \* \* \* \*